United States Patent
Tu et al.

(10) Patent No.: US 11,247,947 B2
(45) Date of Patent: Feb. 15, 2022

(54) METHOD OF HIGH-PRESSURE PURIFICATION OF [F-18]FEONM

(71) Applicant: Institute of Nuclear Energy Research, Atomic Energy Council, Executive Yuan, R.O.C., Taoyuan (TW)

(72) Inventors: Yean-Hung Tu, Taoyuan (TW); Li-Yuan Huang, Taoyuan (TW); Jenn-Tzong Chen, Taoyuan (TW); Tsai-Yueh Luo, Taoyuan (TW); Shiou-Shiow Farn, Taoyuan (TW); Wuu-Jyh Lin, Taoyuan (TW)

(73) Assignee: Institute of Nuclear Energy Research, Atomic Energy Council, Executive Yuan, R.O.C., Taoyuan (TW)

(*) Notice: Subject to any disclaimer, the term of this patent is extended or adjusted under 35 U.S.C. 154(b) by 0 days.

(21) Appl. No.: 17/140,246

(22) Filed: Jan. 4, 2021

(65) Prior Publication Data

US 2021/0147315 A1     May 20, 2021

Related U.S. Application Data

(63) Continuation-in-part of application No. 16/261,780, filed on Jan. 30, 2019, now abandoned.

(51) Int. Cl.
| | | |
|---|---|---|
| *C07B 63/00* | (2006.01) | |
| *B01J 20/284* | (2006.01) | |
| *C07B 59/00* | (2006.01) | |

(52) U.S. Cl.
CPC ............ *C07B 63/00* (2013.01); *B01J 20/284* (2013.01); *C07B 59/001* (2013.01); *C07B 2200/05* (2013.01)

(58) Field of Classification Search
None
See application file for complete search history.

(56) References Cited

PUBLICATIONS

Chen Jenn-Tzong, Journal of Engineering Research and Application, vol. 9, Issue 3 (series-V) Mar. 2019, pp. 19-22.*

* cited by examiner

*Primary Examiner* — Clinton A Brooks
(74) *Attorney, Agent, or Firm* — Demian K. Jackson; Jackson IPG PLLC

(57) ABSTRACT

A method is provided to purify [F-18]FEONM under a high pressure. The synthesis processes of [F-18]FEONM are integrated. An isolation process of non-toxic radio-high performance liquid chromatography (radio-HPLC) is used to purify the crude product. The method integrates a convention [F-18]FDG synthesizer and a novel radio-HPLC system together in a heat chamber. After radiofluorinating the precursor, the reaction product is purified with an alumina solid-phase column in advance to obtain the crude product while fluorine-18 is removed. Then, diphenyl semi-preparative HPLC column is used for a final purification. A non-toxic solvent is used for mobile-phase eluting to remove the unreacted precursor and the phase-transfer solvent. The radiofluorination has a reaction yield about 50 percent (%). The method has an uncorrected radiochemical yield of 10~20%. Both of the radio-HPLC and the radio-thin layer chromatography (radio-TLC) have radiochemical purity higher than 95%.

7 Claims, 5 Drawing Sheets

METHOD OF HIGH-PRESSURE PURIFICATION OF [F-18]FEONM

TECHNICAL FIELD OF THE INVENTION

The present invention relates to purifying [F-18]FEONM; more particularly, to a non-toxic production, where purification using no toxic solvents is processed with precursor removed under the same state; and the final product can be directly injected into animal/human through intravenous injection for positron emission tomography (PET).

DESCRIPTION OF THE RELATED ARTS

Cerebral blood flow/metabolism inspection of nuclear medicine provides data of change in brain functions. With the information on anatomical changes obtained through traditional computed tomography (CT), effects complemented with each other are provided. In particular, profound values are found in diagnosing diseases like cerebral vascular accident (CVA), transient ischemic attack (TIA), epilepsy, dementia, etc. As for other applications, such as head trauma and mental diseases, positive reports are also found.

Regarding current nuclear medicine brain scanning, the most commonly used developers are categorized into uses for blood flow and glucose metabolism these two kinds. Recently, PET is promoted to replace single-photon emission computed tomography (SPECT). In the United States, few hospitals use technetium-99m (Tc-99m) SPECT scanning. Most hospitals use the higher-level glucose positron brain scanning (F-18 Fluorodeoxyglucose, FDG) to replace the conventional developer labeling Tc-99m. The PET can process imaging in a shorter time and provide higher resolution images and brain metabolic information. However, the FDG drugs require to be produced by a cyclotron. Examinations are not so generally applied that the cost of the developer is high. Since the production process is not non-toxic, the prepared product cannot be directly used in intravenous injection.

A prior art is U.S. Pat. No. 9,789,207. In the prior art, after fluorine-18 (F-18) ions are added into amino polyether to process azeotropy two times, a precursor is added for fluorination and, then, flows through a solid-phase extraction column for purification to obtain a product. Although this patent is a [F-18]FEONM process, the precursor used and the production process are not for high-pressure purification.

Hence, the prior arts do not fulfill all users' requests on actual use.

SUMMARY OF THE INVENTION

The main purpose of the present invention is to process purification using no toxic solvents with precursors removed under the same state, where, as compared to the traditional [F-18]FDDNP analogue which needs to complete a primary purification with a solvent having higher toxicity and solid-phase extraction is further processed to reduce the content of relevant elution solvents, the present invention effectively shortens the production time, increases the recycling ratio and reduces the content of solvent having higher toxicity used for production.

Another purpose of the present invention is to provide a non-toxic purification process, where the generated product is non-toxic; the non-toxic solvent—ethanol—is used to elute the product for obtaining an injection by direct dilution; and intravenous injection can be directly applied owing to non-toxicity.

Another purpose of the present invention is to extend the use of the present invention to PET to obtain application potential, where the product has dual radiographies of two Alzheimer disease-related proteins with simultaneous imaging.

To achieve the above purposes, the present invention is a method of high-pressure purification of [F-18]FEONM comprising steps of: (a) radioflourinating a precursor (TEONM) to produce a crude product of [F-18]FEONM; (b) injecting the crude product of [F-18]FEONM with an injector and a semipreparative diphenyl column via semi-preparative high pressure pumping unit to isolate and purify such that a mobile-phase is obtained with an ethanol solution and wherein said (TEONM) precursor is eluted under a flow speed of 1.6 milliliters per minute (ml/min) and when the operating pressure is up to 700 psig; (c) filter sterilizing remaining crude product of [F-18]FEONM obtained after eluting said (TEONM) precursor to obtain a purified product of [F-18]FEONM. Accordingly, a novel method of high-pressure purification of [F-18]FEONM is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

Figure 1:
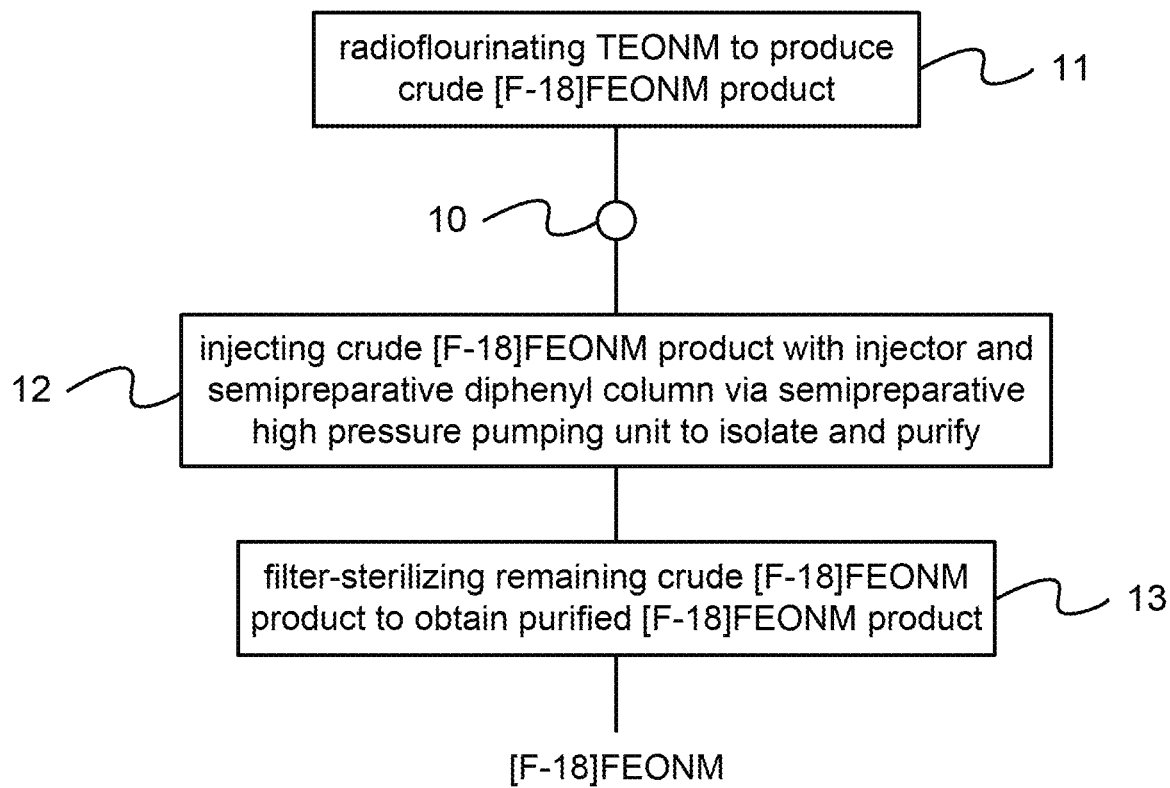
FIG. 1 is the flow view showing the preferred embodiment according to the present invention.

The following description of the preferred embodiment is provided to understand the features and the structures of the present invention.

[F-18]FEONM is a naphthol derivative and also an analogue of [F-18]FDDNP, which is especially designed for positron emission tomography (PET) and has a lipophilicity higher than [F-18]FDDNP and a novel effective agent as Tau Tangle developer. The present invention integrates the synthesis processes of [F-18]FEONM, where a non-toxic radio-high performance liquid chromatography (radio-HPLC) isolation process is used to purify a crude product of [F-18] FEONM. The method integrates a conventional [F-18]FDG synthesizer and a novel radio-HPLC system together in a heat chamber. After radiofluorinating a precursor, the product is purified with an alumina solid-phase column in advance to obtain the crude product with fluorine-18 (F-18) removed. Then, a diphenyl semipreparative HPLC column is used for final purification. A non-toxic solvent is used for mobile-phase eluting to remove the unreacted precursor and the phase-transfer solvent. The radiofluorination has a reaction yield above 50 percent (%). The non decay corrected radiochemical yield of the whole process is—10~20%. Both of the radio-HPLC and the radio-thin layer chromatography (radio-TLC) have radiochemical purities higher than 95%.

Please refer to FIG. 1 to FIG. 5, which are a flow view showing a preferred embodiment according to the present invention; a view showing brain uptake biodistribution ratios of [F-18]FEONM in a 12~13 month-old P301S/PS19 transgenic mouse model; an HPLC view showing a precursor and a reference; a view showing UV absorption peaks of a precursor after radiofluorination; and a view showing an analysis result of radiochemical purity of [F-18]FEONM. As shown in the figures, the present invention is a method of high-pressure purification of [F-18]FEONM, comprising the following steps:

(a) Radiofluorination 11: A precursor (TEONM) is obtained to process radiofluorination.

(b) High-efficiency liquid-phase isolation and purification 12: A crude product of [F-18]FEONM obtained after processing the radiofluorination is injected with an injector 10 to process isolation and purification through semipreparative high pressure pumping unit. Therein, a semipreparative diphenyl column, which has a size of 250×10 millimeters (mm), is used to process the isolation and purification through HPLC; a mobile-phase is obtained with a 95% ethanol solution; and the precursor is eluted under a flow speed of 1.6 milliliters per minute (ml/min) and when the operating pressure is up to 700 psig.

(c) Filter sterilization 13: The crude product of [F-18] FEONM obtained after eluting the precursor is processed through filter sterilization to remove impurities and mycoplasmas for forming a product of [F-18]FEONM purified; and the product of [F-18]FEONM obtained after the filter sterilization is stored in a sterile glass vial. Therein, the product of [F-18]FEONM purified has a functional group of —$C_2H_4O$— at an end of F-18 to obtain lipophilicity. Thus, a novel method of high-pressure purification of [F-18] FEONM is obtained.

Figure 2:
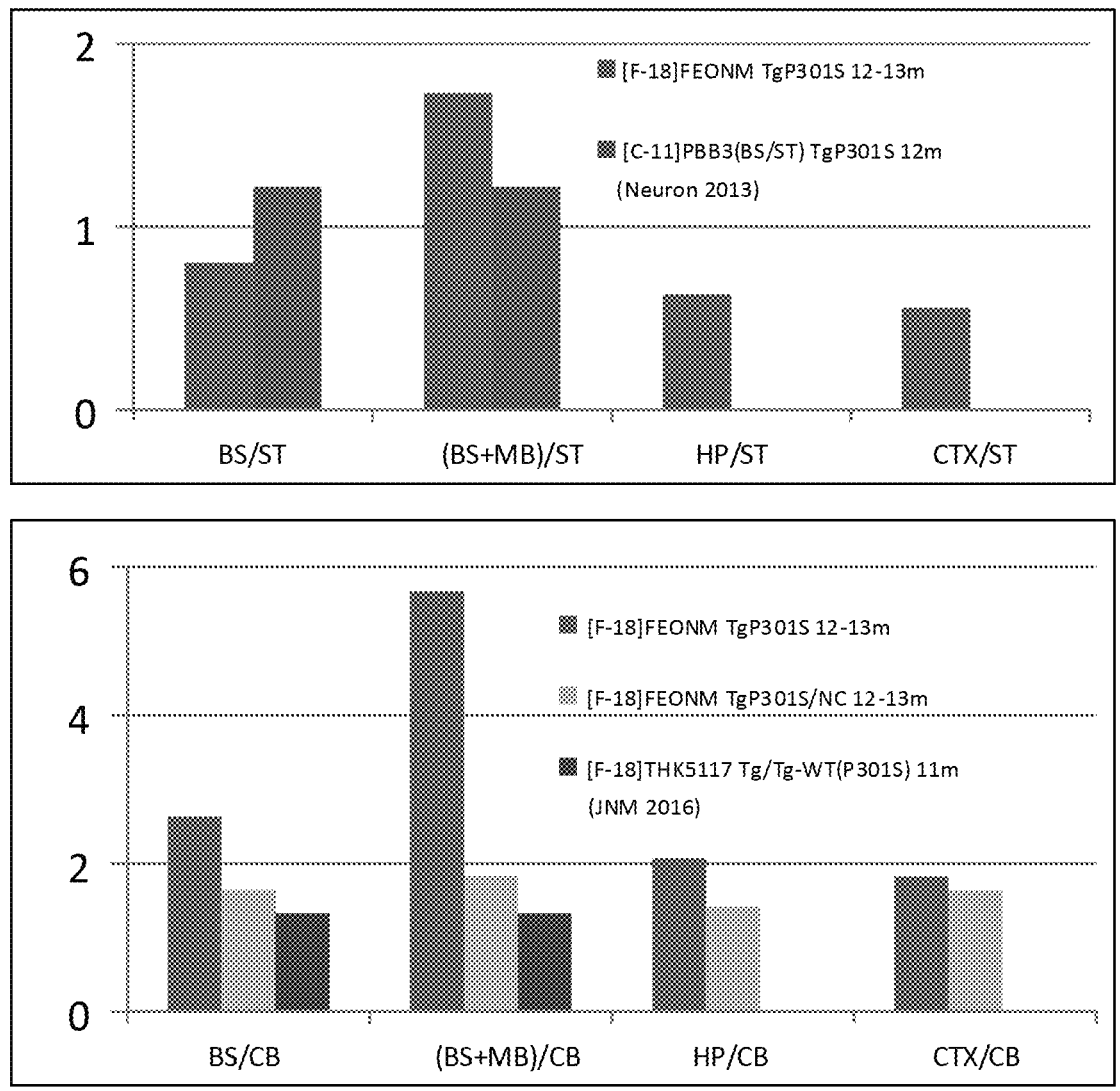
FIG. 2 is the view showing the brain uptake biodistribution ratios of [F-18]FEONM in the 12~13 month-old P301 S/PS19 transgenic mice.

FIG. 2 shows brain uptake biodistribution ratios of [F-18] FEONM in 12~13 month-old P301S/PS19 transgenic mice, where [F-18]FEONM is purified through an alumina solid-phase extraction column; BS means brainstem; ST means striatum; MB means midbrain; HP means hippocampus; CTX means cortex; and CB means cerebellum. It can be found in the result shown in the figure that the product of [F-18]FEONM is effective to Alzheimer disease stages.

Figure 3:
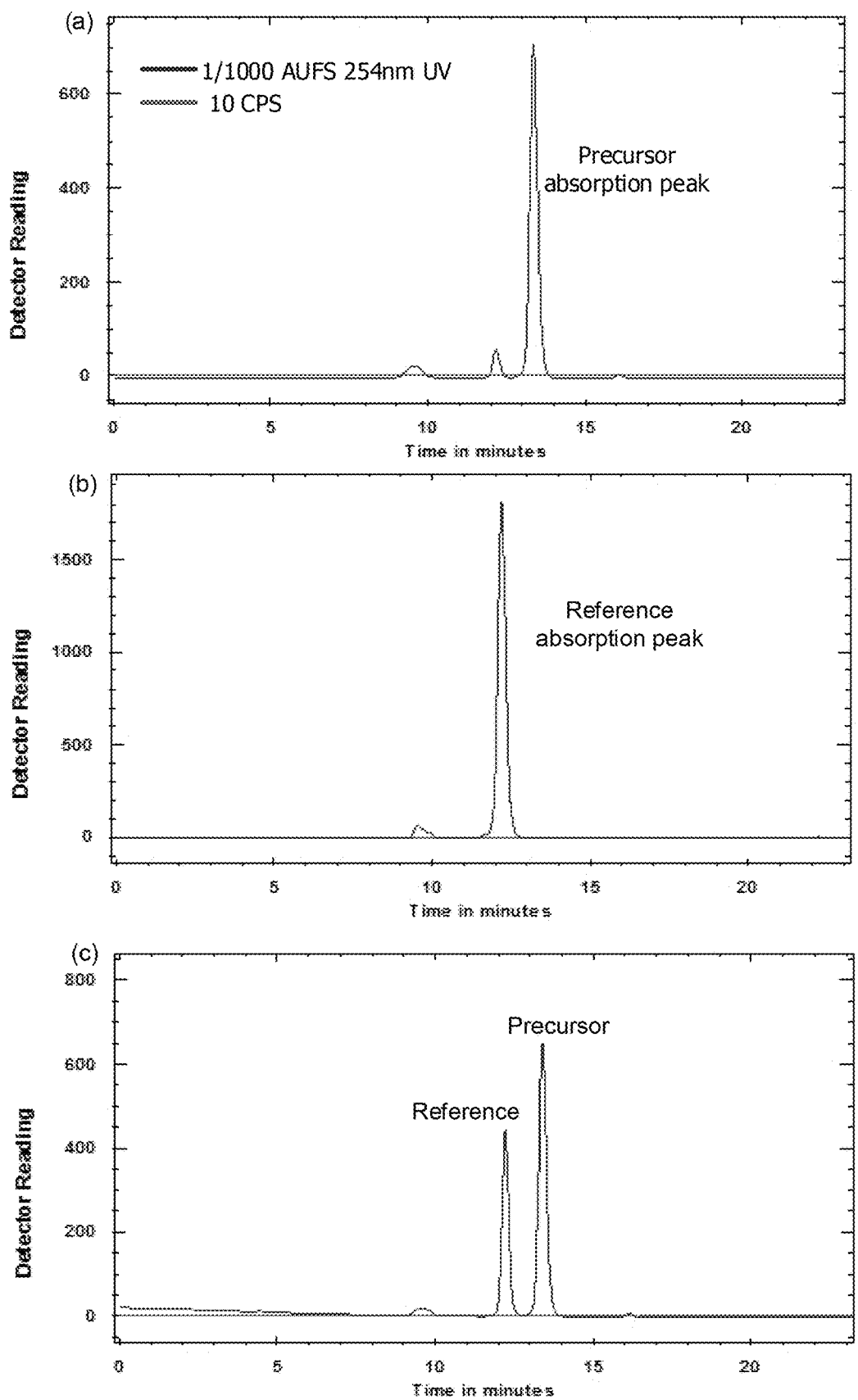
FIG. 3 is the high performance liquid chromatography (HPLC) view showing the precursor and the reference.

The isolation work for the precursor and the reference is the foundation work in the present invention. In FIG. 3, the present invention detects the retention time of a precursor and a reference as shown in diagram (a) and diagram (b), respectively, where a radio-HPLC system is used with carbon-18 (Germini C-18), silicone, and a hydrophilic interaction chromatography (HILIC) column to mix the precursor and the reference for separating them with a mobile phase of acetonitrile and ethanol. Yet, both the diagrams show the same retention time before using the diphenyl column no matter whether the reference is added or not. This may be due to their structural similarity, where the main difference is that fluorine comes from oxygen. [F-18] FEONM has a retention time for about 12 minutes (min). The precursor has a retention time for about 13 min, which is eluted with 95% of ethanol under 1.6 ml/min by using a semipreparative diphenyl column. Although the retention time differs for 1 min only, the UV absorption peaks of TEONM and FEONM as the precursor and the reference for [F-18]FEONM do not overlap in FIG. 3. Thus, the present invention applies this phenomenon in isolation with a product collector of an automated synthesizer to successfully isolate the precursor and the reference for ensuring the precursor be removed through fraction during collecting the final product.

Figure 4:
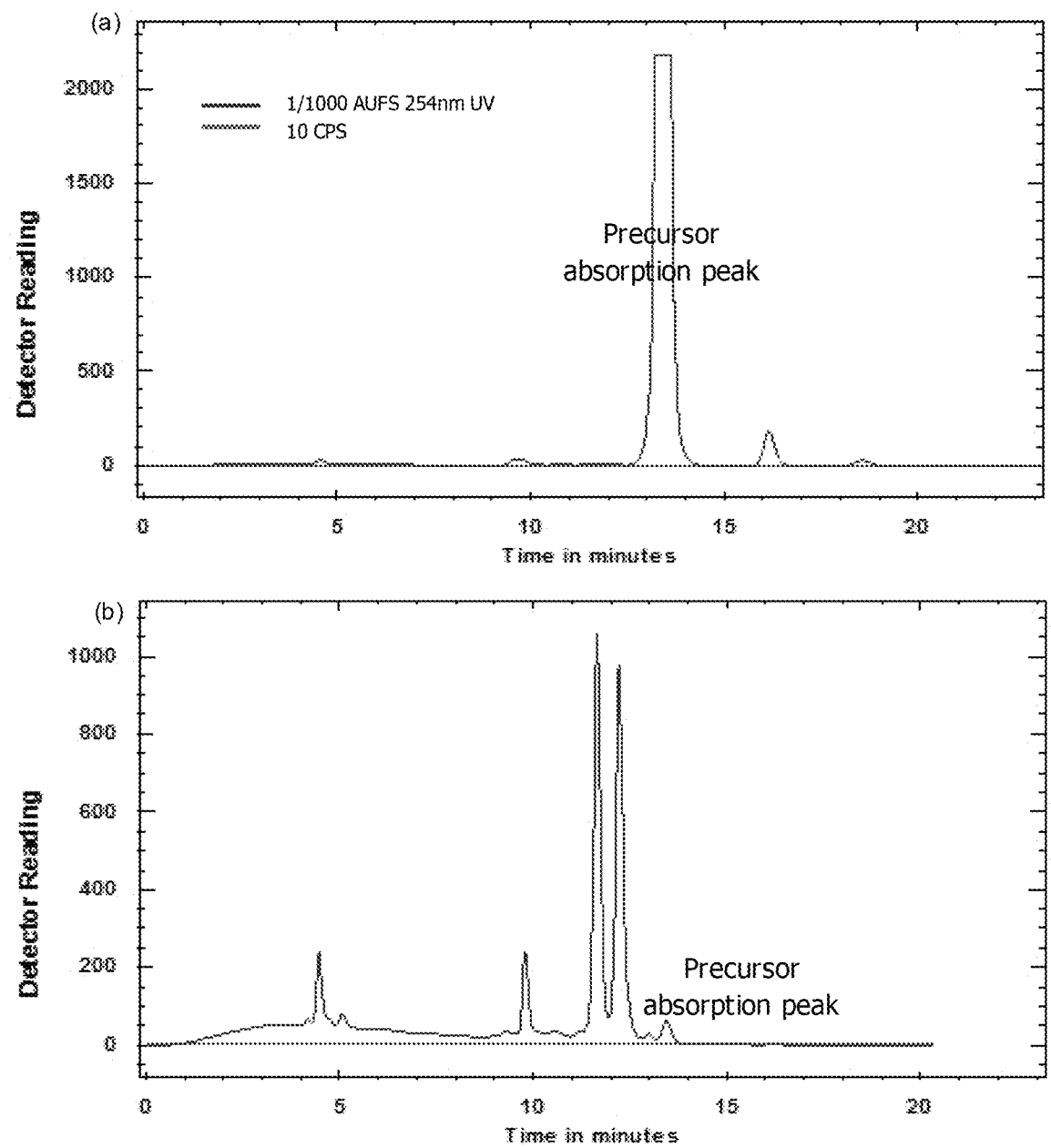
FIG. 4 is the view showing the ultraviolet (UV) absorption peaks of the precursor after radiofluorination.

As compared to a precursor of nitroaromatic compound like nitrophenyl derivatives, [F-18]FEONM and its precursor TEON are relatively unstable. Hence, during the radiofluorination at high temperature, the precursor may degrade. In FIG. 4, the same volumes of the precursor and the crude product are injected. Therein, diagram (a) shows the precursor of [F-18]FEONM added, whose amount (5 mg) exceeds the detecting limit of a UV detector; and diagram (b) shows that the UV absorption peaks of the radiofluorinated precursor are greatly lowered. It means that, because the precursor is greatly decomposed in the radiofluorination, the UV peaks (retention time: 13 min) are very low when the same volumes of the precursor and the crude product are injected. This means most precursors are degraded during the reaction. Because its molecular structure has a toluenesulfone leaving group, the precursor is greatly degraded during the radiofluorination at high temperature. This is a situation totally different from the precursor of nitroaromatic compound, which has a resonant structure binding nitro and diphenyl ring with resonant electron orbit having strength affordable to resist the breaking of covalent bond happened on another molecule during fluorination. The degraded compound of the toluene-sulfone precursor can be read from the UV absorption view, whose peak starts at 3 min and retention time is 11 min. The nearest by-product retention time is 11 min, which is the impurity most difficult to be removed in the product and whose amount is controlled as a specification of the final product for chemical impurity. The final product of [F-18]FEONM is collected through fraction with the eluting solution for radio-HPLC. The final product has a radiochemical yield of 10~20%. The radiochemical purity is detected through radio-HPLC (C-18 column, eluting with 95% acetonitrile) and radio-TLC (silica gel plate, mobile phase of 95% acetonitrile). The detecting result show that the radiochemical purities are both higher than 95%.

Figure 5:
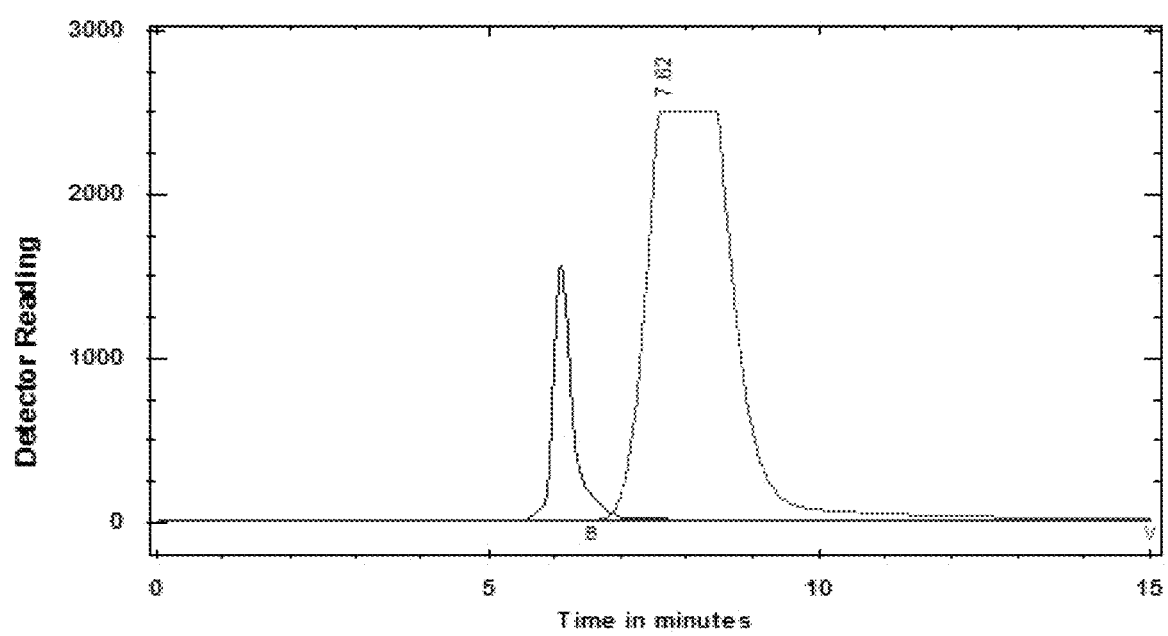
FIG. 5 is the view showing the analysis result of the radiochemical purity of [F-18]FEONM.

FIG. 5 shows the radiochemical purity of the final product of [F-18]FEONM. Diagram (a) shows an analysis result for radio-HPLC, where the column used in HPLC is Cogent C18 100A 5 micrometers (μm), 150×4.6 millimeters (mm); and the eluent is 95% acetonitrile, 0.3 ml/min. Diagram (b) shows an analysis result for radio-TLC, where the plate used in TLC is Merck TLC Silica gel 60 F254; and the eluent is 95% acetonitrile. As shown in the figure, the results are radio- and non-radio-products with no precursors, which is a good effect obtained by the present invention.

As is described above, based on the detection for the high-pressure isolation and purification, the result obtained by the present invention shows the use of ethanol as an eluent in the novel high-pressure isolation and purification successfully removes the precursor to improve chemical purity and simultaneously remove the organic solvent. Besides, the present invention further designs a novel naphthol analogue, [F-18]FEONM, with lipophilicity increased. After the same shake-flask gold standard detection, its lipophilicity is higher than [F-18]FDDNP, as shown in Table 1. This is consistent with the concept of the structure design for the present invention. By adding a —$C_2H_4O$— functional group to a F-18 end, the lipophilicity of [F-18] FEONM is increased to obtain a potential novel brain imaging agent. The present invention develops the high-pressure isolation and purification to achieve the purpose of purification of [F-18]FEONM without toxic compounds.

TABLE 1

|  | [F-18]FDDNP | [F-18]FEONM |
|---|---|---|
| Log P | 1.93 ± 0.10 | 2.20 ± 0.17 |

The whole production of [F-18]FEONM in the present invention is combined with a conventional [F-18]FDG synthesizer and an extra radio-HPLC system. By successfully developing the purification condition of a diphenyl semi-preparative HPLC column, the final product may be collected with no content of precursors, which is more advantageous than the semipreparative HILIC and HPLC columns revealed in previous studies. As compared to other HPLC columns, the high-pressure purification of [F-18]FEONM proposed in the present invention is a non-toxic process and the generated product is also non-toxic, where the non-toxic solvent—ethanol—is used to elute the product for obtaining an injection by direct dilution; and intravenous injection can be directly applied owing to non-toxicity. Therefore, after diluting the elution solution of ethanol from 95% to 20% by adding normal saline, the final product can be directly injected into animal through intravenous injection for PET. Hence, the present invention can extend its use to PET to obtain application potential; and the product has dual radiographies of two Alzheimer disease-related proteins by simultaneous imaging.

To sum up, the present invention is a method of high-pressure purification of [F-18]FEONM, where purification using no toxic solvents is processed with precursors removed in the same state; and, as compared to the traditional [F-18]FDDNP analogue which needs to complete a primary purification with a solvent having higher toxicity and solid-phase extraction is further processed to reduce the content of relevant elution solvents, the present invention effectively shortens the production time, increases the recycling ratio and reduces the content of solvent having higher toxicity used for production.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of high-pressure purification of [F-18]FEONM comprising steps of:
    (a) radioflourinating a precursor (TEONM) to produce a crude product of [F-18]FEONM;
    (b) injecting the crude product of [F-18]FEONM with an injector and a semipreparative diphenyl column via semipreparative high pressure pumping unit to isolate and purify such that a mobile-phase is obtained with an ethanol solution and wherein said (TEONM) precursor is eluted under a flow speed of 1.6 milliliters per minute (ml/min) and wherein the operating pressure is up to 700 psig;
    (c) filter sterilizing remaining crude product of [F-18]FEONM obtained after eluting said (TEONM) precursor to obtain a purified product of [F-18]FEONM.

2. The method according to claim 1, wherein said radiofluorination has a reaction yield of higher than 50 percent (%).

3. The method according to claim 1, wherein said ethanol solution is obtained through diluting ethanol from 95% to 20% by adding normal saline.

4. The method according to claim 1, wherein, in step (c), a filtering cartridge is used to filter said product of purified [F-18]FEONM to remove impurities and mycoplasmas and wherein said purified [F-18]FEONM obtained after said filter sterilization is stored in a sterile glass vial.

5. The method according to claim 4, wherein said filtering cartridge has a filtering size of 0.15~0.25 micrometers (μm).

6. The method according to claim 1, wherein said product of purified [F-18]FEONM has a radio-chemical yield of 10~20% and a radio-chemical purity higher than 95%.

7. The method according to claim 1, wherein, after said (TEONM) precursor is processed through said radiofluorination, an alumina solid-phase extraction column is used to remove F-18 from said crude product of [F-18]FEONM.

* * * * *